United States Patent [19]

Blacklock

[11] Patent Number: 5,716,215
[45] Date of Patent: Feb. 10, 1998

[54] MACHINABLE POST AND CORE

[76] Inventor: Gordon D. Blacklock, 3321 Columbia NE., Albuquerque, N. Mex. 87107

[21] Appl. No.: 567,036

[22] Filed: Mar. 15, 1996

[51] Int. Cl.⁶ .................................................. A61C 8/00
[52] U.S. Cl. .................................... 433/173; 433/172
[58] Field of Search ............................... 433/172, 173, 433/174, 220, 166

[56] References Cited

U.S. PATENT DOCUMENTS

| | | | |
|---|---|---|---|
| 2,735,181 | 2/1956 | Carpenter | 433/166 |
| 2,793,438 | 5/1957 | Ashkin | 433/166 |
| 5,052,929 | 10/1991 | Seal | 433/173 |
| 5,073,110 | 12/1991 | Barbone . | |
| 5,135,395 | 8/1992 | Marlin | 433/173 |
| 5,238,405 | 8/1993 | Marlin | 433/173 |
| 5,316,477 | 5/1994 | Calderon . | |
| 5,350,301 | 9/1994 | De Buck . | |
| 5,350,302 | 9/1994 | Marlin . | |
| 5,407,359 | 4/1995 | Balfour et al. | 433/173 |
| 5,564,923 | 10/1996 | Grassi et al. | 433/173 |

*Primary Examiner*—Ralph Lewis
*Attorney, Agent, or Firm*—Terrance L. Siemens

[57] ABSTRACT

A post and core for dentures which is machinable to adjust for axial misalignment of a denture with respect to surrounding dentures or teeth. The core has excess material which is machined away by a dental practitioner to result in a core appropriately oriented to compensate for the misalignment. The unnecessary material projects from the core to form a pie slice or wedge configuration. The pie slice or wedge tapers to a maximum cross sectional area with increasing distance from the post. The included angle of the wedge does not exceed thirty degrees when the post is hexagonal. The novel configuration of the core minimizes volume of material which must be removed by tedious hand machining to result in a core which is appropriately angled with respect to the post in order to overcome the misalignment.

2 Claims, 3 Drawing Sheets

MACHINABLE POST AND CORE

BACKGROUND OF THE INVENTION

1. Field of the Invention

The present invention relates to a post and core assembly for dental implants. More particularly, the post and core assembly is constructed such that the core is intentionally oversized with respect to an associated prosthesis. This enables a dentist to adjust for misalignment from a preferred axial orientation of the prosthesis with respect to the anchor. The oversized post and core assembly is inserted into the anchor, and observed for correctness of angular relationship. Compensation for angular adjustment is performed by machining the core as is appropriate. The machined core is simultaneously reduced in diameter to dimensions appropriate for the prosthesis. The prosthesis is then supported on the modified post and core in a desired axial orientation with respect to neighboring teeth and prostheses.

2. Description of the Prior Art

When a denture is to be implanted into the jaw of a patient, it must be properly aligned with the other teeth or dentures so as to be parallel thereto. A problem arises when an anchor receiving the post and core is inserted into the jaw at an angle not corresponding to a direction resulting in axially correct orientation of the associated denture. This may arise because accurate placement of the anchor within the jaw is extremely difficult to achieve.

It is possible to adjust a denture or prosthesis to compensate for an anchor set out of proper axial alignment with respect to its associated denture.

One approach to this problem has been to provide a post and core having excess material, some of which is selectively removed by machining to leave remaining a post oriented appropriately to compensate for the misalignment. This is shown in U.S. Pat. No. 5,316,477, issued to Luis O. Calderon on May 31, 1994. However, a very great amount of material must be machined away to produce a usable post and core. By contrast, the member including excessive material incorporates a configuration which is not radially symmetrical about the axis of the post and core. The instant configuration is unlike that of Calderon, and greatly minimizes machining regardless of inclination of the post, if inclination is required. Also, Calderon's post and core must have an anchor having a circular hole for receiving the core, and enabling adjustment by rotation of the core within the anchor. By contrast, the present invention has a conventional hexagonal post which cooperates with a conventional anchor having hexagonal hole.

A rotatably adjustable post and core assembly employing reference marks is shown in U.S. Pat. No. 5,350,302, issued to Vincent De Buck on Sep. 27, 1994. The post and core are provided as two separate, subsequently united structures in this invention. By contrast with the device of De Buck, in the present invention, the post and core is unitary both prior to and after machining. Also, De Buck's post member has no excessive material to be removed by machining.

An even more complicated built up post and core assembly is described in U.S. Pat. No. 5,350,302, issued to Gerald M. Martin on Sep. 27, 1994. Some of the components of the post and core assembly have screw bores and mounting cavities which are misaligned, so that the component can be screwed to a supporting component, and a subsequently mounted member continues at an angle to the supporting component. The various components allow for progressive adjustment to suit conditions as successive components are assembled and oriented at new angles to their predecessors. Unlike the present invention, the Martin device is assembled in the desired angular relationship. By contrast, the present invention includes excess material which is removed by machining. This feature is absent in the Martin device.

U.S. Pat. No. 5,073,110, issued to Noram K. Barbone on Dec. 17, 1991, illustrates a post and core assembly wherein the post comprises the ball of a ball and socket joint. The anchor provides the socket. Unlike the present invention, which employs a conventional hexagonal post compatible with a conventional anchor having a hexagonal hole, the anchor of the Barbone device is configured to receive a ball. The Barbone anchor must be designed from the outset to cooperate with its associated post and core. Unlike the present invention, Barbone's apparatus lacks excess material at the post for machining.

None of the above inventions and patents, taken either singly or in combination, is seen to describe the instant invention as claimed.

SUMMARY OF THE INVENTION

The present invention provides a post and core which includes excess material which is removed by machining to result in a post appropriately oriented with respect to the core for existing conditions. The member having the excess material is so configured that a post inclined with respect to axial alignment with the core is possible. Thus, a first correction is provided which inclines the post to compensate for misalignment of the anchor with respect to a vertical direction, with respect to other teeth or dentures.

The invention also provides for a second correction in which the anchor is misaligned angularly on its axis, with respect to other teeth or dentures. This misalignment is that which would result from the post being oriented as if rotated on the axis of the core. This latter correction allows for similar alignment of the new denture with existing teeth or dentures with respect to the front of the mouth, even if the anchor is misaligned in both respects simultaneously.

Of course, the post and core assembly of Calderon, having a large volume of excessive material, could be machined to result in a post appropriately oriented relative to the core so as to address both defective alignments. However, it is an important goal to minimize the tedious hand machining required in removing the excess material. It is relatively easy and inexpensive to form the post and core to include an arbitrary configuration by an initial casting process than it is to modify the initial configuration by subsequent machining. Therefore, the novel post and core assembly is carefully designed so that minimal volume of excessive material is provided, while still enabling machining which allows the above recited adjustments to orientation of the post with respect to the core.

To these ends, the core has excess material projecting therefrom, configured advantageously to minimize machining. The configuration has the appearance of a wedge in plan, but is tapered to have a minimal diameter proximate the post.

This configuration succeeds since it relies on the fact that the post and core assembly can be rotated relative to the anchor. In a conventional anchor having a hexagonal hole for receiving the post, the post and core assembly can be rotated in increments of sixty degrees. If correction in pointing the new denture is required in a magnitude exceeding sixty degrees, the novel post and core assembly is rotated until the correction lies within a value of thirty degrees to the left or right of the existing, faulty orientation. Machining the final core from the excessively sized initial configuration results in the final adjustment to assure correct alignment to the front.

For reasons of economy and convenience to the dental practitioner, then, it is desirable that the novel post and core assembly cooperate with a conventional anchor. It is also desirable to cooperate with conventional denture fabrication techniques and materials.

Inclination from the vertical is also accommodated by the novel configuration of the core. The novel core is narrowest proximate the post, and allows for greater deviation from the vertical with increasing distance from the post. Yet the tapered configuration minimizes machining to achieve this inclination.

Accordingly, it is a principal object of the invention to provide a post and core assembly which has a sufficient volume of excess material at the core for machining a final post therefrom of correct orientation with respect to the post.

It is another object of the invention to minimize the volume of material which must be machined from the core.

It is a further object of the invention to enable an inclined core to be machined from the novel post and core.

Still another object of the invention is to enable a core to be machined which is correctly oriented to enable its associated denture to be properly mounted to the anchor with respect to the front of the mouth.

An additional object of the invention is to provide a machinable core and core assembly which cooperates with a conventional anchor.

It is again an object of the invention that the core and core be rotatably adjustable with respect to and constrained against rotation within a conventional anchor.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
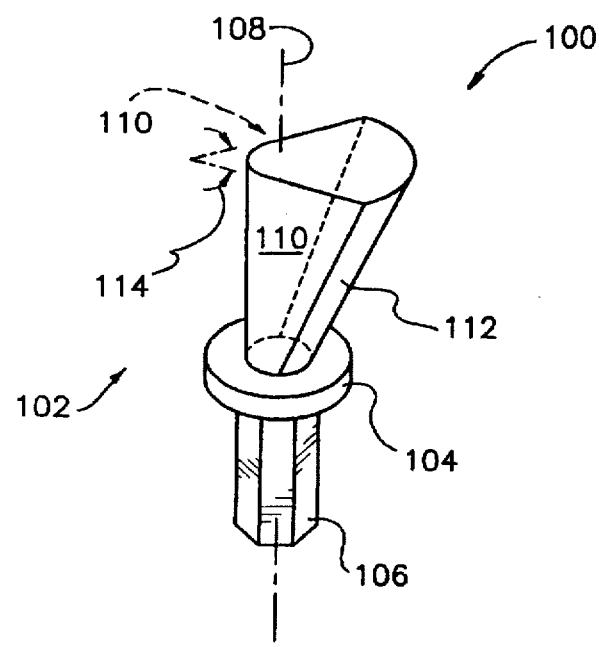
FIG. 1 is a perspective view of the invention.

As shown in FIG. 1A of the drawings, novel core and core assembly 100 is a machinable core and core for fitting a denture 10 (see FIG. 6) to an anchor 12 (see FIG. 6) implanted within bone tissue of a person's jaw (not shown). Post and core 100 is seen to comprise a core 102 connected to a base 104 and in turn to a hexagonal post 106.

Core 102 is circular proximate base 104 and hence core 106, but generally assumes the configuration of a wedge at its upper extremity. Post and core 100 has a longitudinal axis 108, two flat lateral faces 110, and a peripheral surface 112. Lateral faces 110 lie in planes which are parallel to axis 108 and which intersect one another. An included angle 114 is formed between the planes of lateral faces 110.

Figure 6:
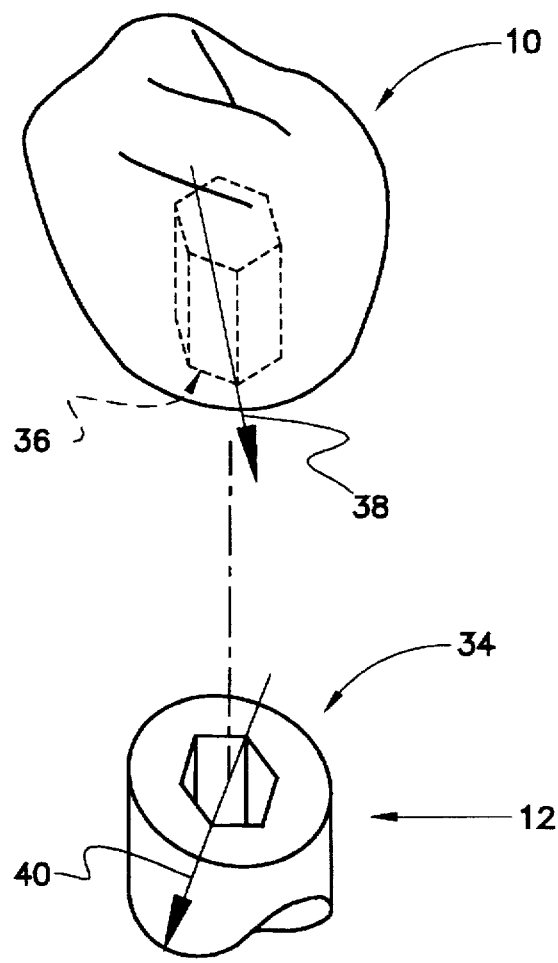
FIG. 6 is an exploded, perspective view of the environment of the invention, but omitting the invention.

The unique configuration of core 102 may be contrasted to a known prior art post and core assembly shown in FIG. 6 of Calderon, U.S. Pat. No. 5,316477 including excess material which is removed by machining. Note base 24 of Calderon shows continuous threads instead of the keying surfaces of this invention.

Figure 2:
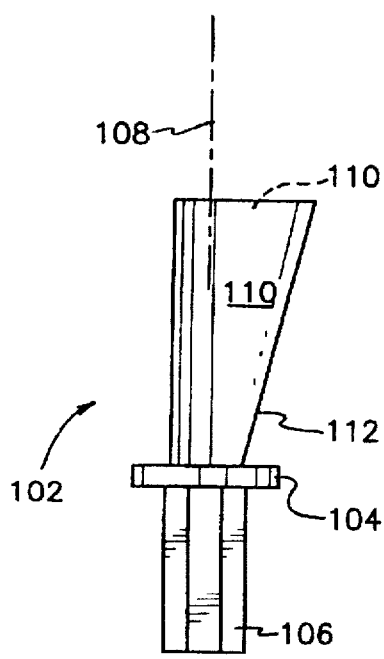
FIG. 2 is a side elevational view of the invention.
Figure 3:
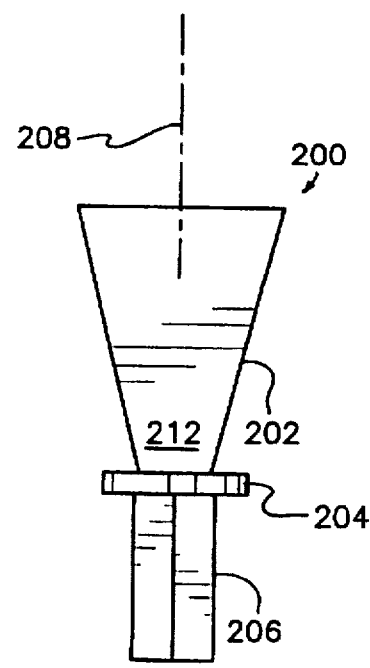
FIG. 3 is a front elevational view of an alternative embodiment of the invention.

Referring now to FIG. 2, post and core 100 is viewed in side elevation. A second embodiment of post and core assembly 200 is shown in FIG. 3. Post and core assembly 200 is shown rotated ninety degrees from the depiction of FIG. 2. Post and core 200 has a core 202, base 204, and post 206 which are generally similar to the corresponding parts of post and core 100, except that peripheral surface 212 is flat, while the corresponding surface 112 of FIG. 1 is curved in the manner of a conical post.

Figure 4A:
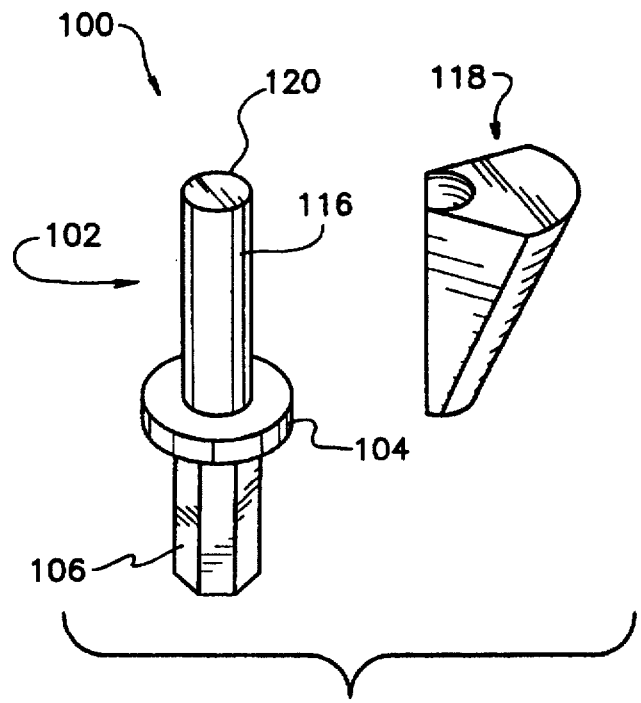
FIG. 4A is an exaggerated, exploded view of the invention, treating a unitary component as if it were two mating parts.

Turning now to FIG. 4A, the advantage of the novel configuration of core 102 becomes apparent. It will be noted that core 102 may arbitrarily be regarded as comprising a central section 116 which is axially aligned with axis 108 of post 106, and a projecting section 118 extending laterally from central section 116. It is important to note that projecting section 118 projects laterally from central section 116 only along a portion of the perimeter 120 of central section 116. There is one, and only one, projecting section 118.

Figure 4B:
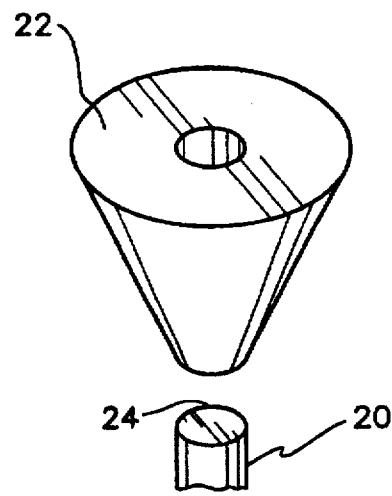
FIG. 4B is an exaggerated, exploded view of the prior art, following the treatment of FIG. 4B, for contrasting the prior art to the present invention.

By contrast, as shown in FIG. 4B, also regarding the prior art core as comprising a central section 20 and a projecting section 22, excess material represented by section 22 projects from central section 20 continuously all along perimeter 24 of central section 20, thereby forming a frustoconical member.

If the desired final configuration of the core of novel post and core 100 corresponds to central section 116 of FIG. 4A, then 118 represents material which must be removed by machining. It is immediately apparent that the greater volume of prior art member 22 (see FIG. 4B) is greater, and requires more time and effort to remove from its corresponding member 20 (see FIG. 4B).

Figure 5A:
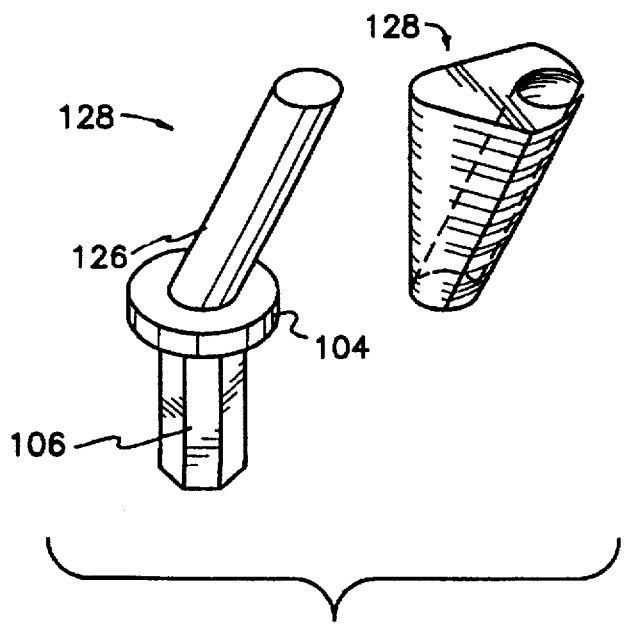
FIG. 5A is a second exaggerated, exploded view of the invention, illustrating one possible machining scheme and symbolically representing material normally comminuted by machining as a unitary or monolithic part.

As illustrated in FIG. 5A, the same advantage of the present invention occurs when the final core must be inclined, or arranged out of axial alignment with post 106, which is a frequently encountered condition. Core 126 is readily machined from core 102 (see FIG. 1) to produce a final post and core 128.

Figure 5B:
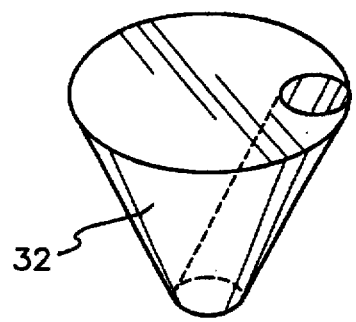
FIG. 5B is a second exaggerated, exploded view of the prior art, illustrating the machining scheme of FIG. 5A, and symbolically representing material normally comminuted by machining as a unitary or monolithic part, for contrasting the prior art to the present invention.

A corresponding procedure employing a prior art post and core requires that a member represented by 32 in FIG. 5B be removed by machining. Again, the prior art post and core 8 will be seen to require that a much greater volume of material need be removed by machining in order to produce a final post and core equivalent to post and core 128 of FIG. 5A.

As clearly seen in FIG. 2, peripheral surface 112 is inclined relative to post 106. Inclination is arranged so that peripheral surface 112 intersects with central section 116 (see FIG. 4A) proximate base 104 and post 106. Inclination causes surface 112 to diverge from central section 116 increasingly with decreasing proximity from base 104 and core 106. This arrangement assures that sufficient material be present in cores 102 and 202, respectively, so that post and core 128 of FIG. 5A may be fabricated from these two embodiments.

FIG. 6 illustrates misalignment of denture 10 with anchor 12 relative to the front of the mouth. In this view, denture 10 includes a preformed opening 36 which is hexagonal merely to emphasize that it can and eventually must be oriented with respect to opening 34 of anchor 12 in order to assure proper forward orientation. Arrow 38 indicates desired orientation of denture 12. However, it will be noted that when a post and core is fitted to denture 10 and inserted into anchor 12, denture 10 will face in the direction of arrow 40.

Figure 7:
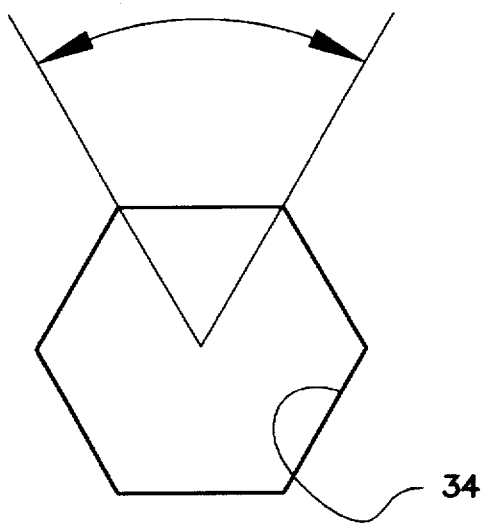
FIG. 7 is a diagrammatic detail view of an environmental component.

In a hexagonal opening 34, rotation of post and core 100 occurs in sixty degree increments. Each such increment will be termed the keying angle, and is illustrated in FIG. 7.

To assure that arrows 38 and 40 are parallel, thus signifying that denture 10 properly points forwardly within the patient's mouth, two adjustments are possible. In the case of a large discrepancy, the novel post and core is rotated in increments of the keying angle, and reinserted into anchor 12. The discrepancy will then be smaller than the keying angle, and is adjusted for by machining.

Angle 114 (see FIG. 1) is of magnitude not exceeding half the magnitude of the keying angle of anchor 12. This relationship assures that with appropriate positioning of post and core 100 within anchor 12 and subsequent machining, any orientation of denture 10 to anchor 12 may be accommodated and compensated for by inclining the core as required.

Figure 8:
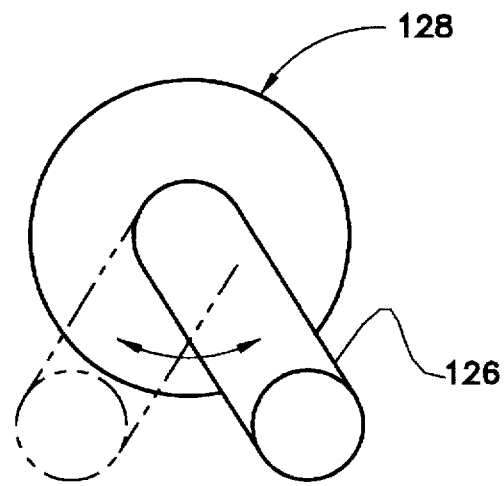
FIG. 8 is a diagrammatic, perspective detail view of the invention.
Figure 9:
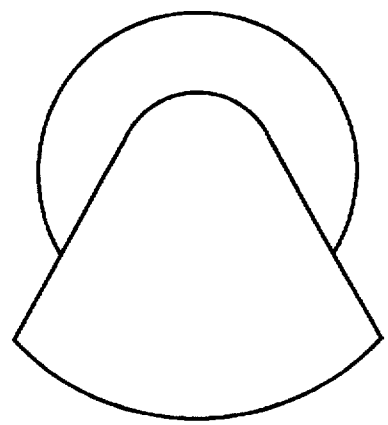
FIG. 9 is a top plan view of the invention.

FIG. 8 illustrates two extreme orientations possible for a final machined core 126 when post and core 100 is oriented as shown in FIG. 9.

Opening 34 may be of configurations other than hexagonal. For example, the configuration may be octagonal, star shaped, gear shaped, or may be still other configurations. Regardless of the selected configuration, a certain number of rotational positions are possible before returning post and core 100 to its original keying angle. The keying angle may be calculated by dividing three hundred sixty degrees by the number of possible different positions of post and core 100 within anchor 12.

Several characteristics of the invention may be varied from the embodiments shown. One characteristic which is not crucial is the circular configuration where core 102 meets base 104, and the related round or cylindrical configuration of central section 116, as depicted in FIG. 4A. Any other configuration, including irregular, would suffice, provided that core 102 and denture 10 will in their final configurations be compatible so that denture 10 can be mounted securely on post and core 100.

Similarly, the post need not be hexagonal, although this configuration is in widespread use in anchors. Given a compatible anchor, the post may be star shaped, gear shaped, or configured in still other ways. It is merely necessary that the post be insertable into the anchor and that mutual rotation therebetween be precluded. This arrangement is referred to herein as keying the post and core within the anchor. Flat surfaces of the hexagon, or equivalent surfaces in the event that the post is other than hexagonal, are referred to as keying surfaces regardless of their actual configuration.

Flat configuration of the uppermost surface of the core is not crucial, nor is the presence of base 104, which is merely traditional.

Also, the lateral faces of the core need not be flat and planar. This characteristic is presented in order to better illustrate relationship between the keying angle and the angle formed by lateral faces 110. Nonetheless, this configuration may well result in easier fabrication and in easier calculation by a dental practitioner of the angle of orientation of a final post and core assembly.

It is to be understood that the present invention is not limited to the embodiments described above, but encompasses any and all embodiments within the scope of the following claims.

I claim:

1. A machinable post and core assembly for fitting a denture to an anchor, said post and core assembly comprising:

a post having an axis and a plurality of keying surfaces for keying said post and core assembly with the anchor and precluding mutual rotation therebetween; and a core comprising a central section having a perimeter parallel to said axis, said central section axially aligned with said axis of said post and connected to said post, and one and only one projecting section extending laterally from said central section, said projecting section projecting laterally from said central section only along a portion of said perimeter of said central section, said projecting section of said core having a peripheral surface inclined with respect to said axis of said post so as to intersect with said central section of said core proximate said post and to diverge from said central section of said core increasingly with decreasing proximity from said post, said projecting section of said core having flat lateral faces, said flat lateral faces being parallel to said axis of said post, said flat lateral faces intersecting one another and forming an included angle between one another.

2. A machinable post and core assembly for fitting a denture to an anchor, said post and core assembly comprising:

a post having an axis and a plurality of keying surfaces for keying said post and core assembly within the anchor and precluding mutual rotation therebetween; and a core comprising a central section axially aligned with said axis of said post and connected to said post, said central section having a parallel to said axis and one and only one projecting section extending laterally from said central section, said projecting section projecting laterally from said central section only along a portion of said perimeter of said central section, said projecting section of said core having a peripheral surface inclined with respect to said axis of said post so as to intersect with said central section of said core proximate said post and to diverge from said central section of said core increasingly with decreasing proximity from said post, said projecting section of said core having flat lateral faces intersecting one another and forming an included angle between one another, said angle being of magnitude not exceeding half the magnitude of the keying angle of the anchor.

* * * * *